United States Patent [19]

Pothetes

[11] Patent Number: 4,859,515
[45] Date of Patent: Aug. 22, 1989

[54] DEVICE FOR DISPOSING OF SHARP INSTRUMENTS

[76] Inventor: Nicholas L. Pothetes, 8496 S.W. Mohawk, Tualatin, Oreg. 97062

[21] Appl. No.: 245,994

[22] Filed: Sep. 14, 1988

Related U.S. Application Data

[63] Continuation of Ser. No. 70,192, Jul. 6, 1987, abandoned, which is a continuation of Ser. No. 40,872, Apr. 20, 1987, abandoned.

[51] Int. Cl.$^4$ .......................... B32B 3/26; B65D 85/24
[52] U.S. Cl. .................................. 428/40; 428/317.1; 428/317.3; 428/192; 206/365
[58] Field of Search ............. 428/40, 43, 317.3, 317.1, 428/192; 206/365

[56] References Cited

U.S. PATENT DOCUMENTS

| | | | |
|---|---|---|---|
| 3,386,877 | 6/1968 | Skochdopole et al. | 428/314.4 |
| 3,690,999 | 9/1972 | Setzer | 428/40 |
| 3,944,069 | 3/1976 | Eldridge, Jr. | 206/ |
| 4,076,882 | 2/1978 | Fenster | 428/ |
| 4,100,681 | 7/1978 | Hollander | 428/43 |
| 4,302,513 | 11/1981 | Russell | 428/40 |
| 4,457,964 | 7/1984 | Kaminstein | 428/43 |

*Primary Examiner*—Alexander S. Thomas
*Attorney, Agent, or Firm*—Eugene M. Eckelman

[57] ABSTRACT

A body member of protective material has opposite surfaces. One of such surfaces has a pressure sensitive adhesive thereon. The body member is bendable whereby upon placing a sharp instrument to be disposed of on the adhesive surface to stick it in place and bending the body member upon itself into connected fold portions at the adhesive surface, a casing is formed around the instrument to hold it securely between the fold portions and to protect personnel from the sharp portion of the instrument. The adhesive surface of the body member is covered by a removable protective layer until use and in addition an auxiliary protective layer is provided on the body member to further restrict penetration of the sharp instrument through the device during disposal steps. The body member is formed of one piece and is bendable along any line thereof. It is dimensioned so as to receive and hold only a single instrument. It can have a lateral tab portion which serves some useful purposes. The device can be manufactured in end to end tear-off extension which exposes a tab of the removable protective layer when torn off.

2 Claims, 1 Drawing Sheet

U.S. Patent    Aug. 22, 1989    4,859,515
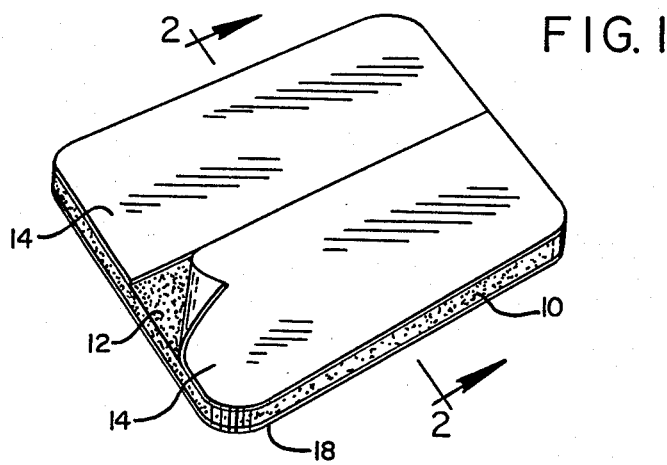
FIG. 1
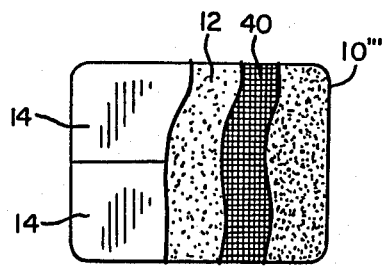
FIG. 10
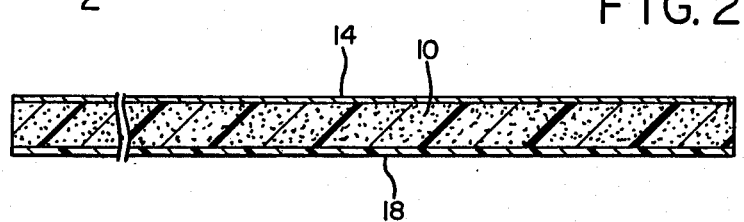
FIG. 2
FIG. 3
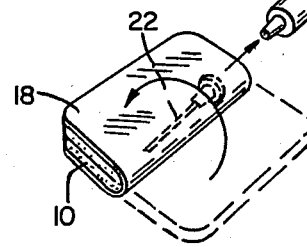
FIG. 4
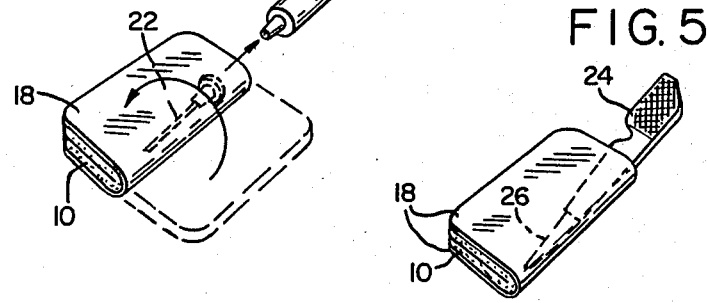
FIG. 4A
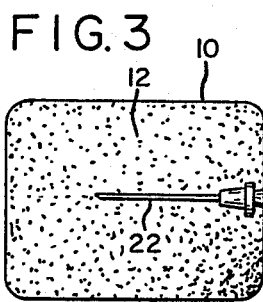
FIG. 5
FIG. 6
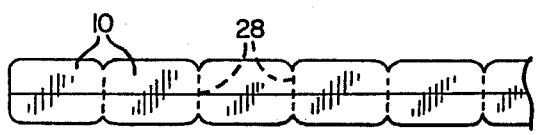
FIG. 9
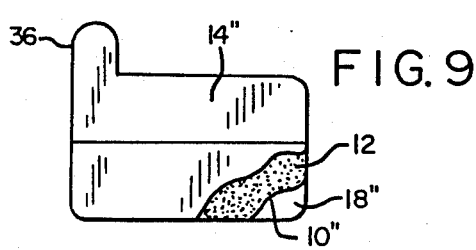
FIG. 7
FIG. 8
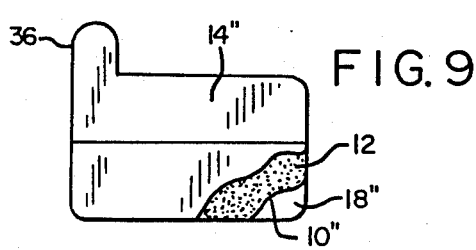

DEVICE FOR DISPOSING OF SHARP INSTRUMENTS

REFERENCE TO PRIOR APPLICATIONS

This application is a continuation of application Ser. No. 070,192, filed July 6, 1987 now abandoned which is a continuation in part of application Ser. No. 040,872, filed Apr. 20, 1987 now abandoned.

BACKGROUND OF THE INVENTION

This invention relates to new and useful improvements in devices for protecting personnel from sharp instruments which are to be discarded.

Accidental needle and scalpel sticks sustained by hospital personnel account for many hospital-related injuries. A high incidence of such injuries occurs in laboratory personnel and nursing and physician personnel. Also, housekeeping personnel often sustain injuries from such source.

Most of these injuries occur after the instruments have been used, thus also subjecting the personnel to serious diseases. Since hypodermic needles and scalpels now commonly used are of the disposable type, one method of discarding them is for medical personnel to deposit the disposables in special containers provided for that purpose or in refuse containers. The carrying of such disposables to the special containers, putting them in the containers, and emptying the containers have proven to be a source of injuries. Placing the disposables in refuse containers is also dangerous to housekeeping personnel since refuse containers are mostly hand emptied.

Another source of disposing or protecting used hypodermic needles has been the use of caps which are placed over the used needle. Here again, such caps are not very safe because the needle must be pointed toward the other hand while directing it into the cap, and almost any kind of miss can result in a needle stick.

Various other means have been employed to receive disposable sharp instruments. One such means is illustrated in U.S. Pat. No. 3,944,069 which is directed to a pad to which a plurality of instruments are stuck. When full the pad is folded shut on a center line and discarded. Another disposal pad is shown in U.S. Pat. No. 4,076,882 directed along a similar concept of sharp instrument disposal as U.S. Pat. No. 3,944,069.

SUMMARY OF THE INVENTION

According to the present invention and forming a primary objective thereof, a device for protecting personnel from sharp instruments is provided that comprises an improvement over existing devices and in particular an improvement over those devices of the type that fold over and enclose the instruments to be discarded.

Another object of the invention is to provide a device for disposing of sharp instruments which for purposes of efficiency in use is of a shape and size to receive only a single instrument, thus assisting medical personnel in detaching the needle or blade from its body portion in convenient and safe manner.

Another object is to provide a device of the type described having a flexible body member of a construction that allows it to be bent in any direction and along any line for accommodating various requirements of the user in enclosing a sharp instrument.

Another object of the invention is to provide a device of the type described which in one form thereof is puncture proof so that a sharp instrument enclosed therein cannot penetrate the walls.

Another object of the invention is to provide a device of the type described which in one form has a laterally extending tab that provides attaching means for the device for temporary support on a convenient surface until such time that the device can be disposed of.

Still another object is to provide a device of the type described that can be inexpensively mass produced and also that can be readily carried on the person.

In carrying out the objectives of the invention, a body member of protective material is provided having one surface covered with pressure sensitive adhesive. The body member is flexible whereby upon placing a sharp instrument to be disposed of on the adhesive surface and bending the body member upon itself into fold portions at the adhesive surface, a casing is formed around the instrument to hold it securely between the fold portions and conceal it, thus protecting personnel from sharp portions thereof. The device has a removable paper layer on the adhesive surface for covering such surface until use and also has an integral auxiliary protective layer to provide barrier means for the sharp instrument. The body member of the device is purposely made of a dimension to receive only a single instrument for convenience and safety reasons and also is constructed so that it can be folded to different shapes to accomplish various purposes not heretofore accomplished. In one form of the invention, the body member has a laterally extending tab for temporary attachment to any convenient surface.

The invention will be better understood and additional objects and advantages will become apparent from the following description taken in connection with the accompanying drawings.

BRIEF DESCRIPTION OF THE DRAWINGS

FIG. 1 is a perspective view of a first form of device employing concepts of the present invention;

FIG. 2 is an enlarged cross sectional view taken on the line 2—2 of FIG. 1;

FIG. 3 is a plan view of the device of FIG. 1 and showing an initial step for enclosing a sharp instrument therein, the instrument illustrated in this view comprising a hypodermic needle;

FIG. 4 is a perspective view showing final steps in enclosing the needle;

FIG. 4A is an end view showing a modified fold arrangement which is available with the present device;

FIG. 5 is a view similar to FIG. 4 but showing application of the present device to disposable scalpels;

FIG. 6 is a fragmentary plan view showing strip manufacture of the present device;

FIG. 7 is a plan view showing another form of manufacture;

FIG. 8 is a side edge view taken from the right side of FIG. 7;

FIG. 9 is a plan view of another form of the invention, a portion of this view being broken away; and FIG. 10 is a plan view of still another form of the invention, a portion of this view also being broken away.

DETAILED DESCRIPTION OF PREFERRED EMBODIMENTS

With particular reference to the drawings, FIGS. 1 and 2 show one form of the product in detail, ready for use. It comprises a body member 10 of a size capable of receiving a sharp instrument flatwise thereon. The top surface 12 of the body member comprises a pressure sensitive adhesive surface, and such surface in manufacture and storage prior to use has a removable protective layer 14 such as a film of thin paper or plastic. Layer 14 may comprise one piece or if desired it may comprise two or more pieces in an arrangement providing a convenient manner of removal. Adhesive surface 12 has only minimal adhesive adherence with the paper for ready removal of the latter but when folded on itself forms a strong, substantially permanent bond.

Body member 10 preferably comprises a closed cell sponge pad of rubber or plastic. Such sponge is light in weight and has suitable thickness, for example, ½ to 4 millimeters, or thicker. The closed cell structure of the body portion 10 makes it substantially moisture proof and somewhat resistant to penetration by sharp instruments.

Also forming a part of the device is a bottom layer 18 which in manufacture is permanently secured as by adhesive bonding to the bottom surface thereof. Layer 18 is of a material which prevents under normal usage the sharpened end of the instrument from protruding through the device during the steps of disposal. For this purpose, layer 18 can comprise a dense rubber or plastic which cannot be penetrated under normal circumstances. At the same time, layer 18 is flexible so that the body member can be readily folded on itself. In a preferred structure, the body member has no fold lines whereby it can be folded randomly as desired by the user, as will be more apparent hereinafter.

FIGS. 3 and 4 show the present device in connection with the disposal of a hypodermic syringe having the usual barrel portion 20 and the usual needle portion 22. The removable layer 14 is first taken off and the syringe then laid on the body member 10 in a position such that the needle is fully or substantially fully engaged with the surface 12. The needle is pressed firmly down on the adhesive surface 12 and it thus sticks firmly thereto. While holding onto the handle or barrel portion 20 of the hypodermic needle with one hand, the operator then folds opposite portions of the body member into engagement with each other to fully enclose the needle. This latter step is shown in FIG. 4. With the use of present day sponge rubber and adhesive, the two fold portions are bonded together and the needle thus permanently encased.

The needle 22 is thus enclosed within the folded body member and personnel handling the disposed hypodermic syringe are protected from needle sticks. The sponge body member 10 resists penetration somewhat of the needle point therethrough but the dense layer 18 stops penetration which will result from normal handling. That is, since the needle extends substantially parallel with the layer 18, even though it would accidentally penetrate the sponge body member, it would in the event of severe mishandling, merely slide along the inner surface of the layer 18 and not penetrate it.

The barrel portion 20 is generally removable from needle portion 22, and if it is desired to break the syringe down for disposal, it is apparent that the adhesive layer firmly encases the needle portion and a good grip can be obtained on the latter without fear of a needle stick. The barrel portion can be readily unthreaded or pulled away from the needle portion. Such separation of the parts is shown in FIG. 4. Also, by selected positioning of the syringe and needle on the surface 12, in an arrangement shown in FIG. 3 wherein the needle portion is fully disposed on such surface, the entire needle portion, including the syringe connecting end, can be enclosed whereby any fluids in the needle are contained within the covering that is formed. Since the body member 10 is moisture proof, such fluids are fully trapped inside and personnel are protected therefrom.

FIG. 5 illustrates that the device may be used with other sharp instruments such as scalpels 24. A blade portion 26 of the scalpel is enclosed within the device in the same manner as the needle portion 22.

FIG. 4A illustrates an important concept of the invention. More particularly, the body member is made without fold lines since it is desired that no fold lines be present to interfere with particular usages of the device. For example, it may be desired to fold the device as shown in FIGS. 4 and 5 wherein it is doubled over approximately along a longitudinal center line thereof; or, if desired it can be folded on a line offset from longitudinal center as in FIG. 4A to form an extension 10a. With this arrangement, an area of adhesive 12 is left exposed and the device can be temporarily stuck to an available surface or appliance until such time that it can be further handled for disposal. This is an important feature in emergencies or when the medical person has his or her hands full. Without a fold line, the body member can also be folded along a lateral line or obliquely.

The dimensions of the device are such that its surface 12 only holds one instrument. Such contributes to easy usage and easy handling. Furthermore, it provides a safe disposal arrangement since other used sharp instruments will not be exposed and in the way. A good size for the intended purpose is approximately 4×5 cm.

FIG. 6 shows one form of manufacturing process wherein body members 10 may be constructed in strip form with a tear line 28 therebetween. The device may thus be supplied in strip or roll form. The body member 10 and backing 18 may be entirely severed and adjacent ones of the guard held together by the paper which contains the tear line 28.

FIGS. 7 and 8 show another manufacturing form. In this form, individual body members 10' are constructed and stamped or cut with a full width extension 30 thereof at one end. The body member 10' and bottom layer 18' of the extension are separable from the main part by means of a full width tear line 32. The tear line 32 also penetrates the paper layer 14' except in a central extension 34 which forms a tab. In other words, tear line 32 does not extend through the tab 34 of the layer 14' but rather extends around the one end thereof whereby the extension 30 of the body member can be torn off along the line 32, leaving the tab 34 to project by itself. In the use of this embodiment by personnel, it is merely necessary to tear off the extension 30 of the body member and grasp the tab 34 for pulling off the removable layer 14'.

With reference to FIG. 9, a further embodiment of the invention includes a lateral tab 36 formed integrally with the body member 10" and the bottom layer 18". The body member and tab have the adhesive surface 12 thereon and paper layer 14" also covers the body member and tab. By means of this embodiment, the tab 36 will project beyond one side of the body member after the latter has been closed on a sharp instrument and thus the device can be stuck by means of such tab to an available surface or appliance until such time that it can be further handled for disposal. Also, the tab can be used to lock the closed device together in addition to the adhesive lock since such tab can be folded over adjoining edges and onto the opposite surface where its adhesive will provide a double lock.

With reference to FIG. 10, an embodiment of the invention is shown which employs a screen barrier layer 40 in the device which provides a more positive barrier against penetration by a sharp instrument than a layer of rubber or plastic 18 which was illustrated in FIG. 1 In this embodiment, there is a body member 10''' comprising a sponge layer to which the barrier layer 40 is integrally attached as by adhesive. The sticky or pressure sensitive surface 12 is applied over the barrier layer 40 for temporarily holding the removable protection layer 14 of paper. Thus, in use, a sharp instrument to be disposed of is laid on the sticky surface 12 of the barrier layer 40 and the device folded over as described in connection with previous embodiments. Also similar to previous embodiments, the FIG. 10 structure has no fold lines and can be folded as desired or necessary.

The barrier layer 40 in FIG. 10 comprises screening, such as metal or plastic screening, of a type and mesh which cannot be penetrated by a needle. A screen mesh size of 1000 openings per square inch, referred to as No. 100 screening, will accomplish such purpose. Smaller screen sizes may be employed if desired. Such screen, in addition to not being penetrable, is very flexible and allows bending of the device along any desired line as described in connection with the FIG. 1 embodiment.

In the FIG. 10 embodiment, wherein the barrier layer 40 is on the upper side of the body member, the latter can be colored on its lower surface whereby when folded such color readily indicates that the device has been folded and is ready to be discarded. It is to be understood that the FIG. 1 embodiment could use the screen layer 40 of FIG. 10 in lieu of bottom layer 18.

In accordance with the invention, an extremely safe and easy to use device is provided for enclosing disposable hypodermic needles and scalpels, or other sharp instruments.

It is to be understood that the forms of my invention herein shown and described are to be taken as preferred examples of the same and that various changes in the shape, size and arrangement of parts may be resorted to without departing from the spirit of my invention, or the scope of the subjoined claims.

Having thus described my invention, I claim:

1. A device for protecting personnel from sharp instruments that are to be discarded, consisting essentially of:

a substantially rectangular flexible body member having side and end edges and opposite surfaces, said body member being constructed of a closed cell sponge for resisting penetration by a sharp instrument, one of said surfaces having a pressure sensitive adhesive thereon capable of forming a secured, substantially permanent bond between overlapping areas of said surface when folded on itself, a protective layer on said pressure sensitive adhesive surface arranged to be removed before said body member is folded on itself, said body member being foldable upon itself with portions of said adhesive surface in engagement whereby upon placing a single sharp instrument to be discarded on said adhesive surface and folding the body member upon itself and said adhesive surface around the instrument, a casing is formed for the instrument to hold it securely between said fold portions and to protect personnel therefrom, said body member being approximately 4×5 cm. in its dimensions and arranged to receive only a single instrument, an auxiliary protective layer of high density, tough flexible material integral with said body member on the opposite surface from said adhesive surface preventing penetration by a sharp instrument, each of said body member and auxiliary protective layer having a uniform uninterrupted thickness throughout its full length and width and being hingedly foldable along any portion of said body member and in any direction, and a lateral tab on said body member projecting beyond one side edge of the body member, said tab member also having a pressure sensitive adhesive thereon and covered by said removable protective layer.

2. A device for protecting personnel from sharp instruments that are to be discarded, consisting essentially of:

a substantially rectangular flexible body member having side and end edges and opposite surfaces, said body member being constructed of a closed cell sponge for resisting penetration by a sharp instrument, one of said surfaces having a pressure sensitive adhesive thereon capable of forming a secured, substantially permanent bond between overlapping areas of said surface when folded on itself, a protective layer on said pressure sensitive adhesive surface arranged to be removed before said body member is folded on itself, said body member being foldable upon itself with portions of said adhesive surface in engagement whereby upon placing a single sharp instrument to be discarded on said adhesive surface and folding the body member upon itself and said adhesive surface around the instrument, a casing is formed for the instrument to hold it securely between said fold portions and to protect personnel therefrom, said body member being approximately 4×5 cm. in its dimensions and arranged to receive only a single instrument.

* * * * *

UNITED STATES PATENT AND TRADEMARK OFFICE
CERTIFICATE OF CORRECTION

PATENT NO. : 4,859,515

DATED : August 22, 1989

INVENTOR(S) : Nicholas L. Pothetes

It is certified that error appears in the above—identified patent and that said Letters Patent is hereby corrected as shown below:

Column 6, line 26,

Claim 2, change the period at the end of the claim to a comma and add the following:

-- and an auxiliary protective layer integral with said body member, said auxiliary protective layer comprising a screening of a structure and mesh size which prevents penetration by a hypodermic needle,

UNITED STATES PATENT AND TRADEMARK OFFICE
CERTIFICATE OF CORRECTION

PATENT NO. : 4,859,515                                Page 2 of 2
DATED      : August 22, 1989
INVENTOR(S) : Nicholas L. Pothetes It is certified that error appears in the above-indentified patent and that said Letters Patent is hereby corrected as shown below:

said auxiliary protective layer being integrally secured to one surface of said body member and said pressure sensitive adhesive being provided on said auxiliary protective layer.

Signed and Sealed this

Eighth Day of February, 1994

Attest:

BRUCE LEHMAN

*Attesting Officer*             *Commissioner of Patents and Trademarks*